(12) United States Patent
Masaki

(10) Patent No.: US 8,652,207 B2
(45) Date of Patent: Feb. 18, 2014

(54) PLUG COMPONENTS FOR BONE TUNNEL

(75) Inventor: Osamu Masaki, Osaka (JP)

(73) Assignee: MMT Co., Ltd., Osaka (JP)

( * ) Notice: Subject to any disclaimer, the term of this patent is extended or adjusted under 35 U.S.C. 154(b) by 202 days.

(21) Appl. No.: 13/159,619

(22) Filed: Jun. 14, 2011

(65) Prior Publication Data

US 2012/0271414 A1 Oct. 25, 2012

(30) Foreign Application Priority Data

Apr. 20, 2011 (JP) ................................. 2011-093764

(51) Int. Cl.
*A61F 2/08* (2006.01)
*A61F 2/28* (2006.01)

(52) U.S. Cl.
USPC ..................................... 623/13.11; 623/16.11

(58) Field of Classification Search
USPC ..................................... 623/13.11–13.2, 16.11
See application file for complete search history.

(56) References Cited

U.S. PATENT DOCUMENTS

| 6,325,804 B1 * | 12/2001 | Wenstrom et al. .......... 623/13.12 |
| 8,012,205 B2 * | 9/2011 | Plouhar et al. ............ 623/13.17 |
| 8,303,967 B2 * | 11/2012 | Clineff et al. ................. 424/400 |
| 2008/0195204 A1 * | 8/2008 | Zhukauskas et al. ...... 623/13.14 |
| 2010/0040686 A1 * | 2/2010 | Masaki et al. ................ 424/484 |
| 2011/0313538 A1 * | 12/2011 | Oh et al. .................... 623/23.61 |

FOREIGN PATENT DOCUMENTS

JP 2002-272756 9/2002

OTHER PUBLICATIONS

Brochures "Neobone", Sep. 2010 and its English translation.
Brochures "Neobone X", Dec. 2009 and its English translation.

* cited by examiner

*Primary Examiner* — Suzette J Gherbi
(74) *Attorney, Agent, or Firm* — Wenderoth, Lind & Ponack, LLP

(57) ABSTRACT

A component for satisfactorily plugging a bone tunnel formed in surgery such as ACL reconstruction by regenerating bone in a space portion of the bone tunnel (e.g., a bone tunnel for an arthroscope). The plug component is made of a calcium phosphate-based material, and includes a porous part having a porosity of 50 to 85%. The plug component has a cylindrical shape such that one of its end surfaces forms an angle of 30 to 60 degrees to its central axis.

4 Claims, 3 Drawing Sheets

PLUG COMPONENTS FOR BONE TUNNEL

CROSS-REFERENCE TO RELATED APPLICATION

The present application claims the benefit of priority from Japanese Patent Application No. 2011-093764 filed on Apr. 20, 2011, the entire contents of which are incorporated herein by reference.

BACKGROUND OF THE INVENTION

1. Technical Field

The present invention relates to a plug component (artificial bone prosthetic material) for use in surgery required to plug a bone tunnel, such as anterior cruciate ligament reconstruction or bone biopsy. The present invention relates to a material for filling bone tunnels of humans or animals, more specifically to a material for filling bone tunnels formed in surgery on ligaments or tendons.

2. Description of the Related Art

Ligaments and tendons are fibrous tissues attached to bones and perform the functions of transmitting mechanical tensile forces, preventing dislocation, guiding joint movement, and acting to transmit muscle forces. However, ligaments or tendons are liable to sustain damage when a heavy load is applied to the knee by injury during sports such as basketball, soccer, handball, volleyball, football, snowboarding, and skiing, traffic injury, work accident, daily movements or the like. Damage to ligaments or tendons lead to joint pain and restriction of physical activity, and ligaments or tendons are less likely to spontaneously recover. Therefore, damage that does not heal by conservative therapy has been conventionally treated by surgery such as ligament reconstruction, ligament repair, syndesmoplasty, tendon reconstruction, tendon repair, or tendinoplasty. If anterior cruciate ligament (ACL) damage is left untreated, hematoma or swelling occurs within the knee joint to reduce stability of the knee. In this case, there is a risk of damage to the meniscus, joint capsule or the like and various symptoms occur (for example, the knee suddenly buckles). If ligament damage is left untreated for a long time, there is a case where joint cartilage is damaged and knee tissue damage becomes irreparable, which may lead to osteoarthritis, in which the knee joint does not normally function. Therefore, ACL reconstruction needs to be performed as soon as possible.

In these surgeries, tunnels are formed in bone, and a ligament or tendon graft material is inserted into the bone tunnels and fixed. After surgery, the graft material is biologically fixed in the bone tunnels to heal. Specifically, ACL reconstruction is performed in the following method. A bone tunnel is drilled in the medial side of the tibia. A torn tendon is reconstructed. It is to be noted that there are two methods for ligament reconstruction. One is a BTB (bone-patellar tendon-bone) method using a patellar tendon auto-graft and the other is a STG method using tendons harvested from the semitendinosus tendon and the gracilis tendon located on the medial and posterior side of the knee. In some cases, an artificial tendon is used. Strings are tied to both ends of a reconstruction ligament, and the reconstruction ligament is passed through the bone tunnels by passing the string through the bone tunnels from the tibial side by pulling the string from the femur side. After the string is passed through the bone tunnels, fixation is achieved on the femur side by an endobutton. The string tied to the reconstructed tendon is pulled while the degree of flexion of the knee is checked to determine the degree of tension to fix the string to the medial side of the tibia. The string emerging from the tibial tunnel is fixed by a screw and a small plate. In this case, the tibial tunnel is not completely filled with the graft material and a defect often remains in the tibial tunnel.

However, when a defect remains in a bone tunnel, it takes a long time to fill the defect with regenerated bone after surgery, or hemorrhage from exposed bone marrow in the bone tunnel causes problems after surgery. Further, the defect remaining in the bone tunnel or blood pooled in the defect has risks such as infection. Moreover, when a reconstruction ligament or tendon is torn again and a second surgery needs to be performed, there is a case where the defect remaining in the bone tunnel becomes a problem to the second surgery.

As a solution to these problems, there is a method for filling a bone tunnel with bone wax or an autologous bone or bone substitute. However, in the case of using bone wax, the post-operative course is not satisfactory and there is also a case where infection or swelling occurs or a tumor occurs. Further, bone wax often serves as a source of infection, and when once infection occurs, bone wax needs to be removed. Moreover, bone wax has the drawback of interfering with bone fusion. There is also a drawback that an autograft needs to be harvested from another part of the body. A bone substitute has been developed as a material for filling a bone defect to promote bone regeneration without injury autologous bone in another part of the body. It is preferable that such a bone substitute has a shape or structure that fits a bone tunnel formed in surgery on ligaments or tendons.

However, it is hard to say that conventional artificial bone prosthetic materials have a shape or structure that fits a bone tunnel. The problems associated with a defect remaining in a bone tunnel cannot be solved when the bone tunnel is filled with a material whose shape or structure does not fit the bone tunnel.

For example, JP-A-2002-272756 discloses a fixing instrument for fixing a reconstruction ligament to a tibia side. However, in such a fixing instrument, a bone tunnel is not satisfactorily plugged.

As described above, ACL reconstruction is performed by transplanting and fixing a reconstruction ligament in bone tunnels formed in the tibia and the femur. However, the bone tunnel is not completely filled with the reconstruction ligament and there is a space left in the bone tunnel. A space remaining in a bone tunnel causes the following problems.

(1) Subcutaneous hemorrhage, pain, and swelling occur due to bleeding from bone marrow in a bone tunnel, and therefore the risk of infection increases.

(2) There has been reported that the incidence of a tendon re-tear after ACL reconstruction is 5 to 10%. A bone tunnel formed in surgery for a first ACL reconstruction becomes an obstacle to surgery for a second ACL reconstruction. When a re-reconstruction is performed, surgery for the second ACL reconstruction needs to be performed in two time periods. First, surgery for transplanting an autologous bone harvested from, for example, an ilium into a bone tunnel formed in surgery for a first ACL reconstruction is performed depending on cases. Then, after the completion of bone fusion, surgery for the second ACL reconstruction is performed. Heavy mental, physical, and economic burdens are placed on a patient.

According to the catalog of NEOBONE®, it is disclosed that when a hydroxyapatite bone substitute having interconnected pores is transplanted into a bone defect, the bone defect is quickly filled with a regenerated bone after transplantation.

According to the catalog of NEOBONE® X, it is disclosed that NEOBONE® X is a combination of hydroxyapatite having interconnected pores and a solid part of hydroxyapatite, and therefore achieves both an increase in strength and induction of bone regeneration.

However, it cannot be said that NEOBONE® and NEOBOEN® X have a shape or structure that optimally fits a bone tunnel formed in surgery on ligaments or tendons. Bone in which bone tunnels are formed in surgery on ligaments or tendons has a structure in which spongy bone that contains bone marrow and is rich in cellular elements is surrounded by a bone cortex having high strength. Therefore, a bone prosthetic material needs to have morphology and strength similar to the structure of the bone. Further, the use of a bone prosthetic material having size, length, and shape that fit a bone tunnel is advantageous for regeneration or repair of bone in a living body.

SUMMARY OF THE INVENTION

1. Problems to be solved by the Invention

An object of the present invention is to provide a component for favorably plugging a bone tunnel formed in surgery such as ACL reconstruction by regenerating bone in a space of the bone tunnel (e.g., a bone tunnel for an arthroscope), in order to solve the above problems.

2. Means for Solving the Problems

The present invention provides a plug member made of a calcium phosphate-based material, which comprises a porous structure having interconnected pores and a porosity of 50 to 85%, and has a cylindrical shape such that its one of bottom surfaces forms an angle of 30 to 60 degrees to its central axis.

3. Effects of the Invention

The plug component according to the present invention provides the following effects.

Risks such as infection can be reduced. In a case where a bone tunnel is left open after surgery or a bone tunnel is filled with bone wax that lacks affinity for living tissue, there are high risks of subcutaneous hemorrhage and pain, swelling, and infection associated with subcutaneous hemorrhage. The plug component according to the present invention has a porous part having a porosity of 50 to 85%, and interpore connections ranged from 10-100 μm in diameter which allows living tissue to invade from pores to pores. This makes it possible to regenerate bone after implantation, achieve early bone regeneration, and reduce risks such as infection and risks associated with hemorrhage, which leads to a reduction in treatment costs.

The use of the prosthetic material according to the present invention makes it possible to fill a bone tunnel with bone in a shorter time after surgery due to early regeneration of bone in the bone tunnel after surgery, reduce hemorrhage from exposed bone marrow in a bone tunnel to reduce pain or swelling after surgery, and reduce risks such as infection caused by a defect in a bone tunnel or blood pooled therein. Further, even when a reconstruction ligament or tendon is torn again and a second surgery needs to be performed, the second surgery can be performed with virtually no problems as long as a bone tunnel formed in first surgery is filled with regenerated bone.

Surgery for a second ACL reconstruction can be performed immediately without secondary surgery. There has been reported that the incidence of re-tear of reconstructed ACL is 5 to 10%. Surgery for the second ALC reconstruction is performed using bone tunnels drilled in first surgery. However, surgery for the second ACL reconstruction cannot be performed when the tibial tunnel is not filled with regenerated bone. Therefore, the tibial tunnel needs to be filled with bone wax, or when the first surgery was completed with the tibial tunnel being left open, the tibial tunnel needs to be filled with a autologous bone harvested from the ilium (bone of the hip) to regenerate bone. In this case, it takes about 3 months to fill the tibial tunnel with regenerated bone, and thereafter, surgery for the second ACL reconstruction can be finally performed. When the plug component according to the present invention is used, its porous part allows bone regeneration and therefore surgery for the second ACL reconstruction can be immediately performed using bone tunnels drilled in the first surgery without performing such secondary surgery as described above. This leads to reductions in treatment costs and burdens on a patient.

Particularly, when the plug member is a combination of a porous part and a solid part, the solid part securely stops hemorrhage and the porous part, which is the only one accepted as supporting bone regeneration, early induces formation of bone tissue and achieves bone regeneration. This makes it possible to reduce risks caused by hemorrhage and to perform a second ACL reconstruction in one time period, which is also effective for reducing treatment costs.

DETAILED DESCRIPTION OF THE INVENTION

Figure 1A:
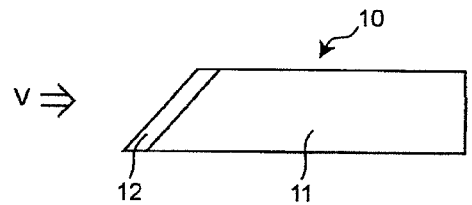
FIG. 1A is a side view depicting a plug component which is a combination of a porous part and a solid part.

A plug component according to the present invention is made of a calcium phosphate-based material (especially, a sintered body of a calcium phosphate-based material), particularly preferably hydroxyapatite and/or β-TCP (β-tricalcium phosphate).

A porous part has a porosity of 50 to 85%, preferably 65 to 80%. If the porosity of the porous part is less than 50%, the ability of the porous part to regenerate bone is significantly reduced. On the other hand, if the porosity of the porous part exceeds 85%, the strength of the porous part is significantly reduced. The term "porosity" refers to a numerical ratio of the capacity of pores to the volume of the porous part expressed as a percentage. The average diameter of interconnections between pores is preferably 10 to 100 μm, particularly preferably 20 to 60 μm. The average diameter of pores is preferably 100 to 300 μm, particularly preferably 150 to 200 μm. Pores interconnect with each other, and pores in a certain surface of the porous part interconnect to pores in the same or different surface of the porous part. The average diameter of interconnections between pores and the average diameter of pores can be measured, for example, by a mercury intrusion porosimeter method and the like.

A solid part has a porosity of preferably 0 to 20%, more preferably 0 to 5%.

The plug component may be constituted only from the porous part, but is preferably formed as a combination of the porous part and the solid part.

A slanted bottom surface portion of the combination is generally constituted from the solid part. In this case, the solid part of hydroxyapatite can be used as a replacement for bone cortex based on the bone shape surrounding a bone tunnel to be filled with the plug component.

The length of a cylinder of the plug component is generally 15 to 70 mm, particularly 20 to 40 mm, and the diameter of bottom surface of the cylinder is generally 3 to 20 mm, particularly 4 to 10 mm (e.g., 4, 5, 6, 7, 8, 9, or 10 mm). In the plug component formed as a combination, the length of the porous part is 15 to 70 mm, and the thickness of the solid part is 1 to 4 mm, particularly preferably 1 to 2 mm. One of the bottom surfaces (slanted bottom surface) of the cylinder forms an angle of 30 to 60 degrees, preferably 40 to 50 degrees, particularly preferably 45 degrees to the central axis of the cylinder. The other bottom surface forms an approximate right angle with the central axis of the cylinder. The use of the plug component formed as a combination makes it possible to regenerate bone in the porous part and to allow the solid part to reinforce the plug component and stop hemorrhage.

The entire or part of the side surface of the cylinder of the plug component (e.g., ⅟30 to ½ (e.g., ⅟20 to ¼) of the side surface) may be tapered such that the other bottom surface has a smaller area. The taper angle is 1 to 40 degrees, for example, 3 to 30 degrees. The diameter of the other bottom surface may be smaller than that of a bone tunnel by 1 to 10 mm, for example, 2 to 6 mm. Such a tapered plug component can be easily inserted into a bone tunnel because the diameter of the other bottom surface is smaller than that of the bone tunnel.

The plug component according to the present invention can be produced in the following process.

A foaming slurry of a calcium phosphate-based material is sintered to obtain a sintered body, and the sintered body is machined to obtain a plug component.

In a case where the plug component is a combination, the porous part and the solid part are preferably molded integrally without providing an adhesive layer. A foaming slurry of a calcium phosphate-based material such as hydroxyapatite is placed in a mold, and then a non-foaming slurry of a calcium phosphate-based material is poured into the mold to combine them with each other. The slurries are dried and then sintered at 800 to 1,400° C., particularly at 1,200° C. to obtain an integrated molded product not containing any component other than a calcium phosphate-based material such as an adhesive.

The plug component according to the present invention can be used in surgery such as ligament reconstruction, ligament repair, syndesmoplasty, tendon reconstruction, tendon repair, or tendinoplasty.

Particularly, the plug component according to the present invention can be properly used in anterior cruciate ligament reconstruction.

The plug component according to the present invention is used in anterior cruciate ligament reconstruction in the following method.

1) A tendon graft for ACL reconstruction is passed through bone tunnels, and is fixed on the femur side. Then, the length of the remaining tibial tunnel not filled with the tendon graft is measured by a special depth gage (the length of a proximal short part of the tibial tunnel is measured).

2) The length of the plug component is adjusted to the measured length of the remaining tibial tunnel by making a cut with the use of a knife or the like and removing an unnecessary part.

3) The plug component whose length has been adjusted to the length of a proximal part of the tibial tunnel is inserted into the tibial tunnel while a string connected to the tendon graft is pulled. Fixation of the plug component does not require a fixing agent or the like, and the plug component can be fixed in the tibial tunnel by contact with bone.

In the present invention, anterior cruciate ligament reconstruction can be performed in the following method.

1. Incisions are made in the skin of the knee to examine the inside of the knee joint with an endoscope. The torn anterior cruciate ligament is removed and the inside of the knee joint is cleaned.

2. A reconstruction ligament is prepared. Patient's own ligament-like tissue is harvested and a reconstruction ligament is prepared. Strings are tied to both ends of the reconstruction ligament harvested from a patient. An endobutton is attached to the end of the one of the strings.

3. A bone tunnel is drilled in the tibia. An incision is made in the skin over the tibia (at a position slightly inside and below the patellar tendon). A bone tunnel is drilled in the tibia from the incision toward a position to which the anterior cruciate ligament has been attached while the inside of the knee joint is observed with the endoscope.

4. A bone tunnel is drilled in the femur from the tibial tunnel toward a position on the femur, to which the anterior cruciate ligament has been attached, to reach the skin of the thigh.

5. The reconstruction ligament is placed. The reconstruction ligament is passed through the bone tunnels by passing the string tied to the end of the reconstruction ligament through the bone tunnels from the tibial side and pulling the string from the femur side. After the string is passed through the bone tunnels, the reconstruction ligament is fixed by anchoring the endobutton to the end of the femur tunnel. Then, if necessary, the ligament is fixed to the tibia by impacting a double spike plate made of a metal into the tibia from the tibial side, and the double spike plate is fixed by a screw.

6. The tibial tunnel is plugged with the plug component. The plug component is placed such that the slanted bottom surface of the plug component coincides with the surface of the tibia.

7. The incisions made in the skin are closed by suturing.

Hereinbelow, the present invention will be described more specifically with reference to the accompanying drawings.

FIG. 1A is a side view depicting a plug component which is a combination of a porous part and a solid part. A plug component 10 is composed of a porous part 11 and a solid part 12. The porous part 11 and the solid part 12 are closely connected with each other by an integrated molding without any adhesive layer using an adhesive. The plug component has a cylindrical shape. As shown in FIG. 1, the bottom surface constituted from the solid part is generally flat, but can have any shape in consideration of the outline of bone. For example, the bottom surface of the solid part may be curved such that its central portion bulges outwardly.

Figure 1B:
FIG. 1B is a front view depicting a plug component which is a combination of a porous part and a solid part.

FIG. 1B is a front view depicting a plug component which is a combination of a solid part and a porous part. FIG. 1B is a view seen from a direction indicated by an arrow V in FIG.

1A. The slanted bottom surface of the cylindrical plug component is constituted from the solid part 12.

Figure 2:
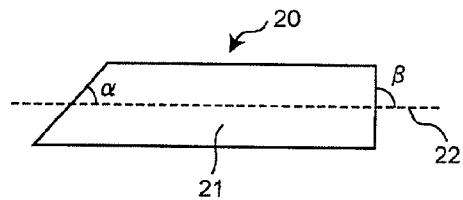
FIG. 2 is a side view depicting a plug component constituted only from a porous part.

FIG. 2 is a side view depicting a plug component constituted only from a porous part. A plug component 20 is constituted only from a porous part 21. The left-hand bottom surface of the plug component 20 forms an angle α with a central axis 22 of the cylinder. The angle α may be in the range of 30 to 60 degrees. The other (i.e., right-hand) bottom surface forms an angle β with the central axis of the cylinder. The angle β may be in the range of 70 to 110 degrees (e.g., 80 to 100 degrees (particularly 90 degrees)).

Figure 3:
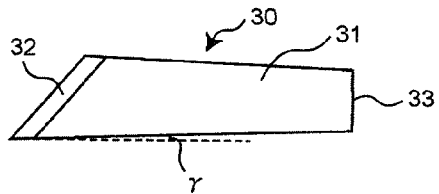
FIG. 3 is a side view depicting a plug component having a tapered shape as a whole.

FIG. 3 is a side view depicting a plug component having a tapered shape as a whole. A plug component 30 is formed from a porous part 31 and a solid part 32. The plug component 30 may be formed only from the porous part 31. The plug component has a tapered shape such that its diameter gradually reduces toward its tip along the entire length of the side surface. A taper angle γ (formed by the side surface of a virtual cylinder and the side surface of the plug component) may be in a range of 1 to 15 degrees (e.g., 3 to 10 degrees). This plug component can be easily inserted into a bone tunnel because the diameter of its bottom surface 33 is smaller than that of the bone tunnel.

Figure 4A:
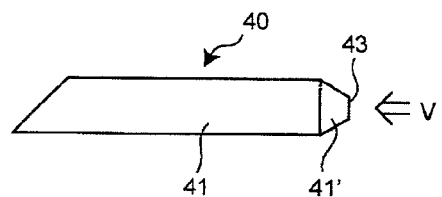
FIG. 4A is a side view depicting a partially-tapered shape of a plug component.

FIG. 4A is a side view depicting a partially-tapered shape of a plug component. The plug component is constituted only from a porous part. The plug component 40 is formed from a porous part 41 and 41'. The plug component may be formed from a porous part and a solid part. The plug component has a tapered shape such that its diameter reduces toward its tip along part of the side surface, and therefore the tapered part of the plug component has a truncated cone shape. A taper angle (formed by the side surface of the cylinder and the side surface of the truncated cone) may be in a range of 5 to 40 degrees (e.g., 10 to 30 degrees). The porous part 41' is first inserted into a bone tunnel when the plug component is used. The porous part 41' has a truncated cone shape and has a bottom surface 43 smaller than the bottom surface of the cylinder. This plug component can be easily inserted into a bone tunnel because the diameter of the bottom surface 43 is smaller than that of the bone tunnel.

Figure 4B:
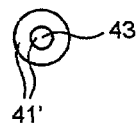
FIG. 4B is a back view depicting a partially-tapered shape of a plug component.

FIG. 4B is a back view depicting a partially-tapered shape of a plug component. FIG. 4B is a view seen from a direction indicated by an arrow V in FIG. 4A. The porous part 41' has the bottom surface 43 of the plug component smaller than the bottom surface of the cylinder.

Figure 5:
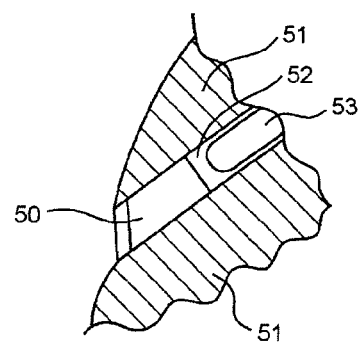
FIG. 5 is a schematic sectional view of a bone tunnel in which a plug component is fixed.

FIG. 5 is a schematic sectional view of a born tunnel in which a plug component is fixed. A tendon graft 53 is inserted in a born tunnel 52 provided in a tibia 51, and a plug component 50 is fixed in the bone tunnel 52 such that the bone tunnel 52 is plugged with the plug component 50. The diameter of the bone tunnel 52 is in a range of 3 to 20 mm, generally 3 to 10 mm.

Hereinbelow, the content of the present invention will be described with reference to the following example. However, the present invention is not limited thereto in any way.

Example 1

A bone substitute prosthetic material shown in FIG. 1 was used in surgery for human knee anterior cruciate ligament reconstruction. Into a bone tunnel (diameter: 6 mm, length: 30 mm), which was formed in the tibia in a direction from the outside of the knee joint toward an anterior cruciate ligament attachment site in the knee joint at an angle of 45 degrees to the axis of the tibia, an autogenous semitendinosus tendon was folded in four was inserted such that a joint-side part of the bone tunnel (length: 15 mm) was filled with the tendon. Then, a defect (length: 15 mm) remaining in the bone tunnel was filled with an artificial bone prosthetic material according to the present invention (diameter: 6 mm, length: 15 mm) having a 3 mm-thick bottom surface prepared from a hydroxyapatite solid part and inclined at an angle of 45 degrees.

Figure 6:
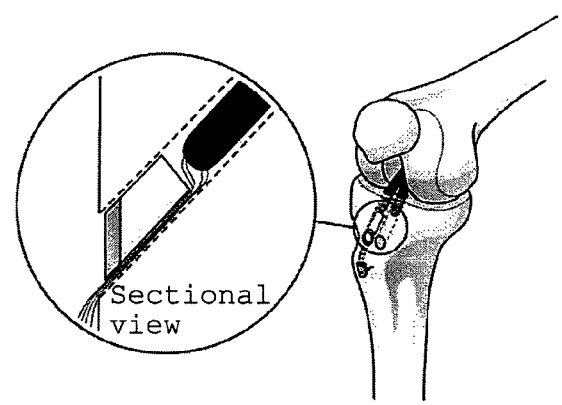
FIG. 6 is a schematic diagram depicting the use of a plug component according to the present invention in anterior cruciate ligament reconstruction.

As shown in FIG. 6, two bone tunnels were drilled in each of the tibia and the femur to prepare and fix reconstruction ligaments using strings. Each of the bone tunnels was plugged with the artificial bone prosthetic material by placing the artificial bone prosthetic material in each of the bone tunnels in such a method that the surface of the solid part of the artificial bone prosthetic material approximately coincided with the surface of the tibia.

Figure 7:
FIG. 7 shows a CT image after surgery for anterior cruciate ligament reconstruction.

A CT image after surgery for the knee anterior cruciate ligament reconstruction is shown in FIG. 7. The image verifies that the slanted bottom surfaces of the plug component coincide with the surface of the tibia and the bone tunnels are satisfactorily filled with the plug component.

The plug component according to the present invention can be advantageously used in surgery required to plug a bone tunnel, such as anterior cruciate ligament reconstruction surgery or bone biopsy.

The invention claimed is:

1. A plug component made of a calcium phosphate-based material, the plug component comprising a porous part having interconnected pores and a porosity of 50 to 85% and a solid part having a porosity of 0 to 20%, the plug component having a cylindrical shape defining first and second end surfaces, wherein the first end surface of the plug component forms an angle of 30 to 60 degrees to its central axis and the first end surface is formed by the solid part.

2. The plug component according to claim 1, wherein the plug component is used for anterior cruciate ligament reconstruction.

3. A method for ligament or tendon surgery comprising filling a bone tunnel with the plug component according to claim 1 such that the first end surface, which is a slanted bottom surface, coincides with a surface of bone.

4. Anterior cruciate ligament reconstruction comprising the steps of:
   i) removing a torn anterior cruciate ligament;
   ii) preparing a reconstruction ligament;
   iii) drilling a bone tunnel in a tibia;
   iv) drilling a bone tunnel in a femur;
   v) placing the reconstruction ligament; and
   vi) filling the tibial tunnel with the plug component according to claim 1.

* * * * *